(12) United States Patent
Blessing et al.

(10) Patent No.: US 9,492,334 B2
(45) Date of Patent: *Nov. 15, 2016

(54) PROCESS FOR PRODUCING ABSORBENT CORE STRUCTURES

(71) Applicant: The Procter & Gamble Company, Cincinnati, OH (US)

(72) Inventors: Horst Blessing, Cincinnati, OH (US); Hans-Adolf Jackels, Mechernich (DE); Markus Rietz, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/331,277

(22) Filed: Jul. 15, 2014

(65) Prior Publication Data

US 2014/0318694 A1    Oct. 30, 2014

Related U.S. Application Data

(63) Continuation of application No. 13/723,308, filed on Dec. 21, 2012, now Pat. No. 8,784,594, which is a (Continued)

(30) Foreign Application Priority Data

Jul. 28, 2004 (EP) ..................................... 04017789

(51) Int. Cl.
*A61F 13/535* (2006.01)
*A61F 13/532* (2006.01)
(Continued)

(52) U.S. Cl.
CPC ....... *A61F 13/535* (2013.01); *A61F 13/15634* (2013.01); *A61F 13/15658* (2013.01);
(Continued)

(58) Field of Classification Search
CPC .............. A61F 13/5323; A61F 13/1568; A61F 13/15658; A61F 13/51476; A61F 13/535
(Continued)

(56) References Cited

U.S. PATENT DOCUMENTS 3,860,003 A    1/1975  Buell
4,009,063 A    2/1977  Wood
(Continued)

FOREIGN PATENT DOCUMENTS

EP    2 032 89 A2    12/1986
EP    0875224 A1    11/1998
(Continued)

OTHER PUBLICATIONS

EP Search report mailed Oct. 16, 2014, 5 pages.
PCT International Search report mailed Oct. 25, 2005, 6 pages.

*Primary Examiner* — Mark A Osele
*Assistant Examiner* — Christopher C Caillouet
(74) *Attorney, Agent, or Firm* — Sarah M. DeCristofaro

(57) ABSTRACT

The present invention is method for forming a sandwich structure having a pattern of particulate material enveloped between a carrier material and a cover material. The method allows accurate forming of pre-determined pattern at high production speed. Such a method is particularly useful in the manufacture of disposable absorbent articles, such as baby diapers.

23 Claims, 7 Drawing Sheets

Related U.S. Application Data continuation of application No. 12/781,901, filed on May 18, 2010, now Pat. No. 8,343,296, which is a continuation of application No. 11/191,507, filed on Jul. 28, 2005, now Pat. No. 7,744,713.

(51) Int. Cl.

| | | |
|---|---|---|
| *A61F 13/15* | (2006.01) | |
| *A61F 13/514* | (2006.01) | |
| *B05C 1/08* | (2006.01) | |
| *B05C 19/04* | (2006.01) | |
| *G06F 17/50* | (2006.01) | |
| *B32B 37/00* | (2006.01) | |
| *B05C 11/10* | (2006.01) | |
| *A61F 13/53* | (2006.01) | |

(52) U.S. Cl.
CPC ... *A61F 13/15764* (2013.01); *A61F 13/15804* (2013.01); *A61F 13/51476* (2013.01); *A61F 13/5323* (2013.01); *B05C 1/0804* (2013.01); *B05C 1/0808* (2013.01); *B05C 1/0817* (2013.01); *B05C 19/04* (2013.01); *B32B 37/00* (2013.01); *G06F 17/5009* (2013.01); *A61F 2013/53051* (2013.01); *B05C 11/1039* (2013.01); *B32B 2250/03* (2013.01); *B32B 2307/726* (2013.01); *B32B 2555/02* (2013.01); *Y10T 156/10* (2015.01); *Y10T 156/1002* (2015.01); *Y10T 156/1007* (2015.01); *Y10T 156/1023* (2015.01); *Y10T 156/1025* (2015.01)

(58) Field of Classification Search
USPC ...... 156/40.1, 196, 199, 209, 210, 276, 459, 156/471–473
See application file for complete search history.

(56) References Cited

U.S. PATENT DOCUMENTS

| | | |
|---|---|---|
| 4,381,783 A | 5/1983 | Elias |
| 4,551,191 A | 11/1985 | Kock et al. |
| 4,610,678 A | 9/1986 | Weisman et al. |
| 4,646,510 A | 3/1987 | McIntyre |
| 4,720,321 A | 1/1988 | Smith |
| 4,741,941 A | 5/1988 | Englebert et al. |
| 4,800,102 A | 1/1989 | Takada |
| 4,834,735 A | 5/1989 | Alemany et al. |
| 4,888,231 A | 12/1989 | Angstadt |
| 4,892,535 A | 1/1990 | Bjornberg et al. |
| 4,994,053 A | 2/1991 | Lang |
| 5,030,314 A * | 7/1991 | Lang ................ A61F 13/15634 156/390 |
| 5,037,416 A | 8/1991 | Allen et al. |
| 5,151,092 A | 9/1992 | Buell et al. |
| 5,213,817 A | 5/1993 | Pelley |
| 5,260,345 A | 11/1993 | Desmarais et al. |
| 5,269,775 A | 12/1993 | Freeland et al. |
| 5,387,207 A | 2/1995 | Dyer et al. |
| 5,397,316 A | 3/1995 | Lavon et al. |
| 5,494,622 A | 2/1996 | Heath et al. |
| 5,554,145 A | 9/1996 | Roe et al. |
| 5,569,234 A | 10/1996 | Buell et al. |
| 5,571,096 A | 11/1996 | Dobrin et al. |
| 5,628,845 A | 5/1997 | Murray et al. |
| 5,662,758 A | 9/1997 | Hamilton et al. |
| 5,830,202 A | 11/1998 | Bogdanski et al. |
| 5,879,751 A | 3/1999 | Bogdanski |
| 5,925,439 A | 7/1999 | Haubach |
| 6,004,306 A | 12/1999 | Robles et al. |
| 6,139,912 A | 10/2000 | Onuschak et al. |
| 6,290,686 B1 | 9/2001 | Tanzer et al. |
| 6,330,735 B1 | 12/2001 | Hahn et al. |
| 6,416,697 B1 | 7/2002 | Venturino et al. |
| 6,529,860 B1 | 3/2003 | Strumolo et al. |
| 6,573,422 B1 | 6/2003 | Rosenfeld et al. |
| 6,610,900 B1 | 8/2003 | Tanzer |
| 6,706,129 B2 | 3/2004 | Ando et al. |
| 6,730,387 B2 | 5/2004 | Rezai et al. |
| 6,802,834 B2 | 10/2004 | Melius et al. |
| 6,811,642 B2 | 11/2004 | Ochi |
| 6,818,166 B2 | 11/2004 | Edwardson et al. |
| 6,832,905 B2 | 12/2004 | Delzer et al. |
| 6,837,281 B2 * | 1/2005 | Spiers .................... B65B 1/366 141/125 |
| 6,923,926 B2 | 8/2005 | Walter et al. |
| 6,972,011 B2 | 12/2005 | Maeda et al. |
| 6,982,052 B2 | 1/2006 | Daniels et al. |
| 7,037,571 B2 | 5/2006 | Fish et al. |
| 7,285,178 B2 | 10/2007 | Mischler et al. |
| 7,598,428 B2 | 10/2009 | Gustavsson et al. |
| 7,750,203 B2 | 7/2010 | Becket et al. |
| 7,767,878 B2 | 8/2010 | Suzuki |
| 7,838,722 B2 | 11/2010 | Blessing et al. |
| 2002/0095127 A1 | 7/2002 | Fish et al. |
| 2002/0102392 A1 | 8/2002 | Fish et al. |
| 2002/0123848 A1 | 9/2002 | Schneiderman et al. |
| 2003/0120249 A1 | 6/2003 | Wulz et al. |
| 2003/0135176 A1 | 7/2003 | Delzer et al. |
| 2004/0127131 A1 | 7/2004 | Potnis |
| 2004/0162536 A1 | 8/2004 | Becker et al. |
| 2004/0236455 A1 | 11/2004 | Woltman et al. |
| 2005/0101929 A1 | 5/2005 | Waksmundzki et al. |
| 2006/0069367 A1 | 3/2006 | Waksmundzki et al. |

FOREIGN PATENT DOCUMENTS

| | | |
|---|---|---|
| EP | 1059072 A2 | 12/2000 |
| EP | 752 892 B1 | 7/2001 |
| EP | 1253231 A2 | 10/2002 |
| EP | 1 403 419 B1 | 5/2006 |
| EP | 1 447 066 B1 | 10/2008 |
| EP | 1621165 A1 | 4/2010 |
| FR | 2 583 377 A1 | 12/1986 |
| JP | 2107250 | 4/1990 |
| JP | 06-191505 | 7/1994 |
| JP | 07-124193 | 5/1995 |
| JP | 08-215629 A | 8/1996 |
| JP | 04-341368 A | 11/1997 |
| JP | 2001-46435 | 9/1999 |
| JP | 11-320742 | 11/1999 |
| JP | 2001-277394 | 10/2001 |
| JP | 2001-321397 | 11/2001 |
| JP | 2002-113800 | 4/2002 |
| JP | 2002-178429 | 6/2002 |
| WO | WO 92/19198 A1 | 11/1992 |
| WO | WO 92/19198 A1 | 11/1992 |
| WO | WO 95/16746 A1 | 6/1995 |
| WO | WO 95/16746 A1 | 6/1995 |
| WO | WO 96/29967 A1 | 10/1996 |
| WO | WO 03/079946 A2 | 10/2003 |
| WO | WO 03/101622 A2 | 12/2003 |
| WO | WO 03/101622 A2 | 12/2003 |

* cited by examiner

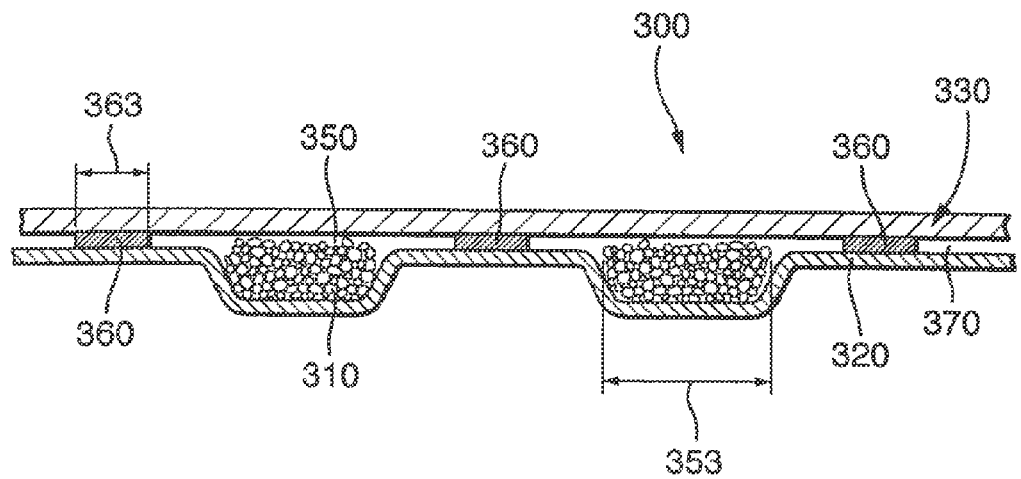
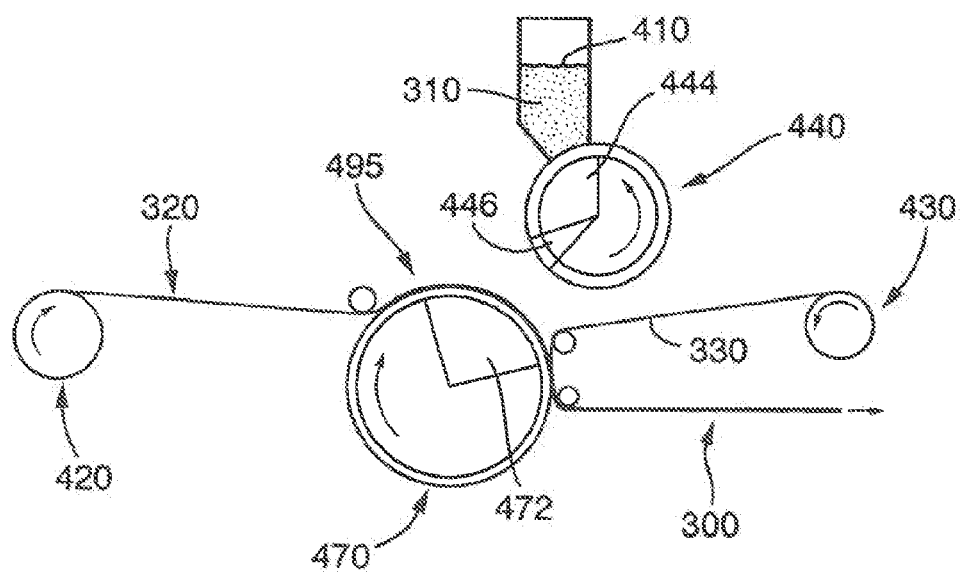

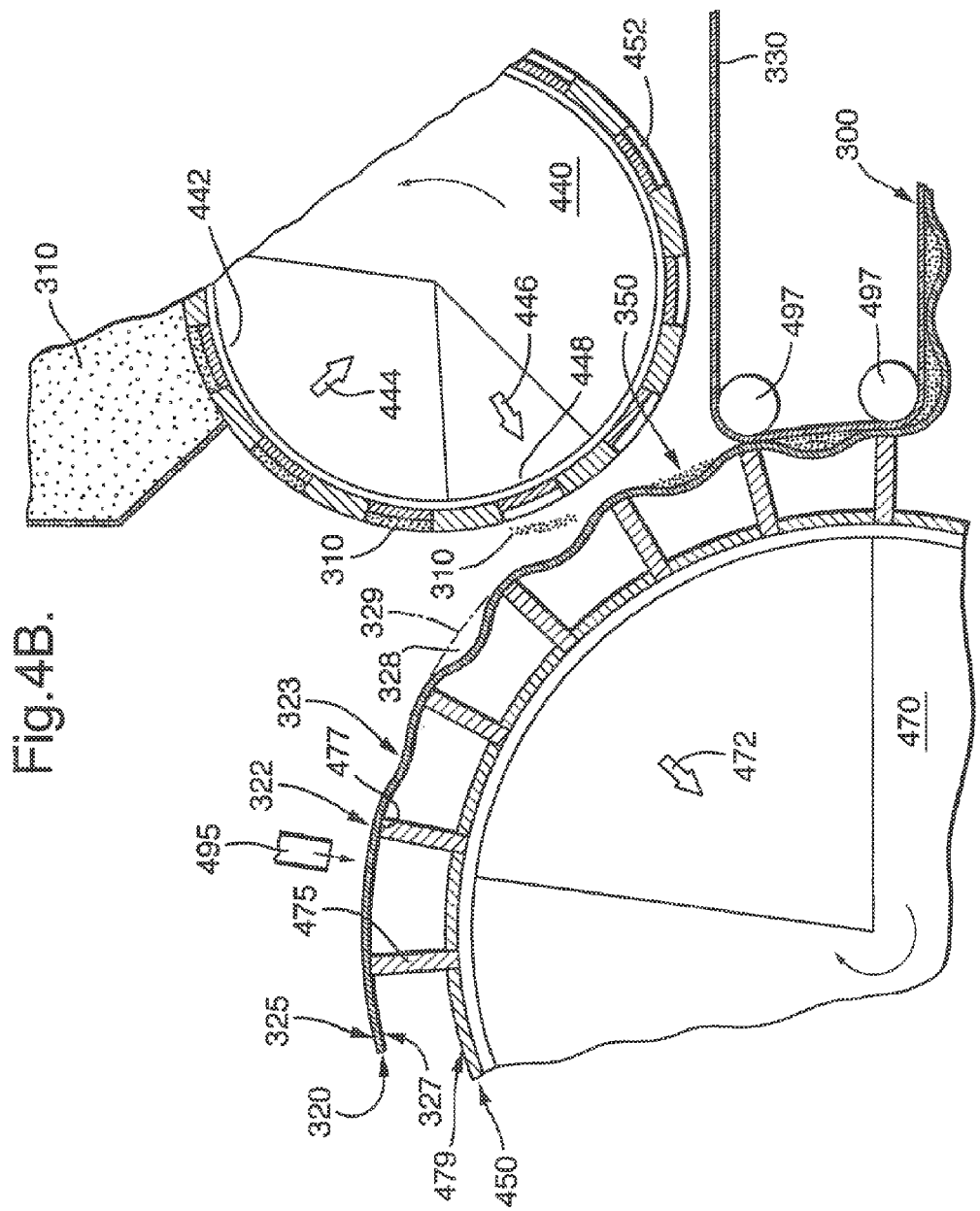

PROCESS FOR PRODUCING ABSORBENT CORE STRUCTURES

CROSS REFERENCE TO RELATED APPLICATION

This application is a continuation of application Ser. No. 13/723,308, filed on Dec. 21, 2012, which is a continuation of application Ser. No. 12/781,901, filed on May 18, 2010, which is a continuation of application Ser. No. 11/191,507, filed Jul. 28, 2005, which are hereby incorporated by reference.

FIELD OF THE INVENTION

The present invention is a process for forming a sandwich structure having a pattern of particulate material enveloped between a carrier and a cover material. In a particular embodiment, the particulate material is super absorbent material, and the sandwich structure is a liquid absorbent structure for use in disposable absorbent products.

BACKGROUND OF THE INVENTION

Composite structures comprising particulate material in a particular pattern are well known in the art, see, e.g. EP-1447066 (Busam et al.; P&G), disclosing an absorbent core for an absorbent article, which has a particulate absorbent material that is immobilized when wet. The absorbent core comprises a substrate layer with an absorbent material, such as an absorbent polymer material.

U.S. Pat. No. 4,381,783 (Elias) discloses an absorbent article with a core comprising pockets of absorbent hydrocolloid material. These pockets are provided to confine the movement of absorbent polymer material, in particular when the article is fully or partially loaded with urine. The pockets form part of an absorbent layer and are typically provided from cellulose material. Hence, as to achieve good immobilization of the absorbent polymer material according to the teaching of this patent relatively high amount of cellulosic material is required. Moreover, the provision of such pockets may hinder the free distribution of liquid to the more absorbent areas of the core, for example the areas of the absorbent polymer materials.

Accordingly, processes to produce absorbent article having a non-homogeneous distribution of absorbent materials such as particulate absorbent polymer material, often referred to as absorbent gelling material or as superabsorbent, are also well known. In WO 03/101622A2 (Tombült et al.; P&G) a pulsing process for creating discontinuous particulate distribution is disclosed, and a similar structure may be produced according to U.S. Pat. No. 5,213,817 (Pelley; McNeill PPC).

Processes aiming at depositing a pattern of particulate absorbent material onto a web are described in U.S. Pat. No. 4,800,102 (Takada; Nordson), employing a rotating mask, or in WO 92/019198A (Perneborn/Mølnlycke) showing a linearly moving mask. FR-A-2583377 (Piron; Colgate Palmolive) discloses a metering drum into which absorbent powder is fed from a hopper for creating discontinuous pattern on a carrier on a conveyor belt. The drum is operated in a step-wise movement.

U.S. Pat. No. 5,494,622 (Heath et al.; K-C), aims at producing pockets of particles in a desired pattern on a web moving at high speed. A pattern chamber is supplied with particles of high absorbency material through which a gas permeable web is transported on a surface having a pattern of openings through which a vacuum is drawn so as to cause the particles to be deposited on the web in the pattern of the openings in the surface. The web carrying the particles is covered by a layer of liquid permeable material or the tension applied to the permeable web is varied to vary the porosity of the web. The particles are held on the web in the desired pattern of pockets while surplus particles between the pockets are removed. The thusly formed pockets form "islands", i.e. they are completely surrounded by bonded regions.

Whilst such documents describe various approaches to the deposition of particulate material onto a surface or on a moving substrate, there is still the need for a method to produce patterned particulate sandwiches in a very well defined pattern and at high production speeds.

SUMMARY OF THE INVENTION

The present invention is a process of creating a sandwich structure comprising particulate material sandwiched between web materials in a very well defined pattern.

The method comprises the step of providing an essentially flat carrier material and an essentially flat cover material for forming the outer sandwich layers, which may be unitary for forming both outer sandwich layers, or which may be different materials forming the outer sandwich layers. Further steps provide an essentially endless support means for the carrier material having a support pattern and a carrier material holding means. The carrier material is positioned over the support means at a carrier speed relative to a fixed frame, whereby the carrier means contacts the support pattern with its support surface and whereby the relative speed between carrier material and the contact surface of the carrier support means is essentially zero. A particulate material is provided and pre-metered. The cover material and the carrier material are combined and affixed by a fixation means with the particulate material positioned there between. The carrier material is supported only in the region of the support pattern of the support means and deformed by a carrier holding means such that indentations are formed in the unsupported regions. The particulate material is transferred to the carrier material into the indentations; thereby forming a primary pattern of particulate material.

In preferred executions, the carrier material is a non-woven material, preferably of the SMS or SMMS type, and it may have a CD-extensibility or a MD-extensibility of more the 20%, preferably more than 100%, but even more preferably not more than 200%. The ratio of MD-extensibility to the CD-extensibility is at a given load not more than one to two. Also the cover material can be a non-woven material, optionally being the same material as the carrier material.

The particulate material can be a bulk material, preferably a superabsorbent, more preferably a partially cross-linked polyacrylate material.

In a preferred execution, the carrier support means is a rotatable drum, preferably having an outer cylinder shell. It is further preferred, that the carrier holdings means is a vacuum air suction.

The carrier support pattern may comprise support pins, which may have a distance of more than 5 mm and not more than 30 mm from each neighboring support pins. The support pins preferably have an outwardly extending surface of at least 0.8 $mm^2$, preferably of at least 4 $mm^2$, but not more than 170 $mm^2$, preferably not more than 80 $mm^2$.

The sandwich fixation means is preferably thermo-bonding or glue-bonding, more preferably a sprayed adhesive.

The bonding region is at least 2%, preferably at least 7%, but more preferably not more than 50% of the area of the pattern area. Preferably, the bonding region comprises essentially no particulate material, as assessed by the method for determining the absence of particles in the bonding area.

The carrier holding means extends the carrier material such that it deforms out of the original flat state forming an indentation. Preferably, the indentations have a volume of more than 30 mm³, preferably more than 100 mm³, but less than about 1000 mm³. Preferably, the particulate material fills more than 5% of the volume of the indentations, preferably not more than 150% of the volume of the indentations.

BRIEF DESCRIPTION OF THE DRAWINGS

FIG. 3B is a cross-sectional view of the sandwich pattern of FIG. 3A.

FIG. 4A is a schematic process diagram for forming a sandwich structure.

FIG. 4B is a schematic enlarged sectional view of a part of the equipment for the process as shown in FIG. 4A.

DETAILED DESCRIPTION OF THE INVENTION

Figure 1:
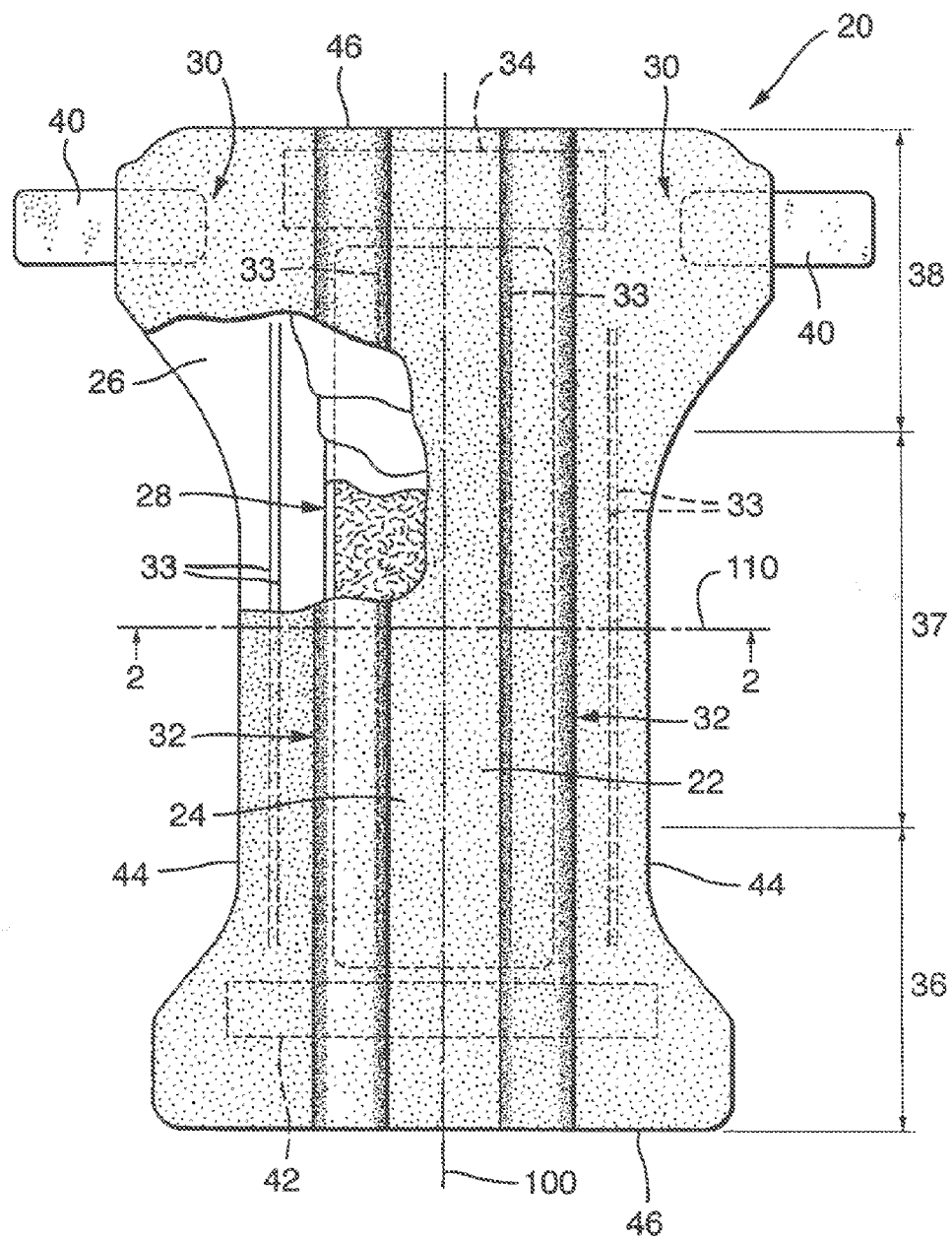
FIG. 1 is a top plan view of a disposable diaper, with the upper layers partially cut away.

The present invention aims at producing a patterned sandwich structure, which contains particulate material being sandwiched between a carrier material in a very well defined amount and pattern. Such structures are particularly useful for disposable absorbent articles. Such articles have very varying requirements as to the desired absorbency depending on the intended use.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Comprise," "comprising," and "comprises" is an open ended term that specifies the presence of what follows e.g. a component but does not preclude the presents of other features, elements, steps or components known in the art, or disclosed herein.

The term "web material" refers to an essentially endless material in one direction, i.e. the longitudinal extension, or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, non-woven/film laminates. Web materials may comprise other materials, such as added binding material, particles, hydrophilizing agents and the like.

The terms "superabsorbent", "super absorbent material" or "SAM", "absorbent gelling material" or "AGM", "absorbent polymer material" are used herein interchangingly, and refer to partially cross-linked polymeric materials, which can absorb water whilst they are swelling to form a gel.

All patents and patent applications (including any patents which issue thereon) assigned to the Procter & Gamble Company referred to herein, are hereby incorporated by reference to the extent that it is consistent herewith.

Figure 2:
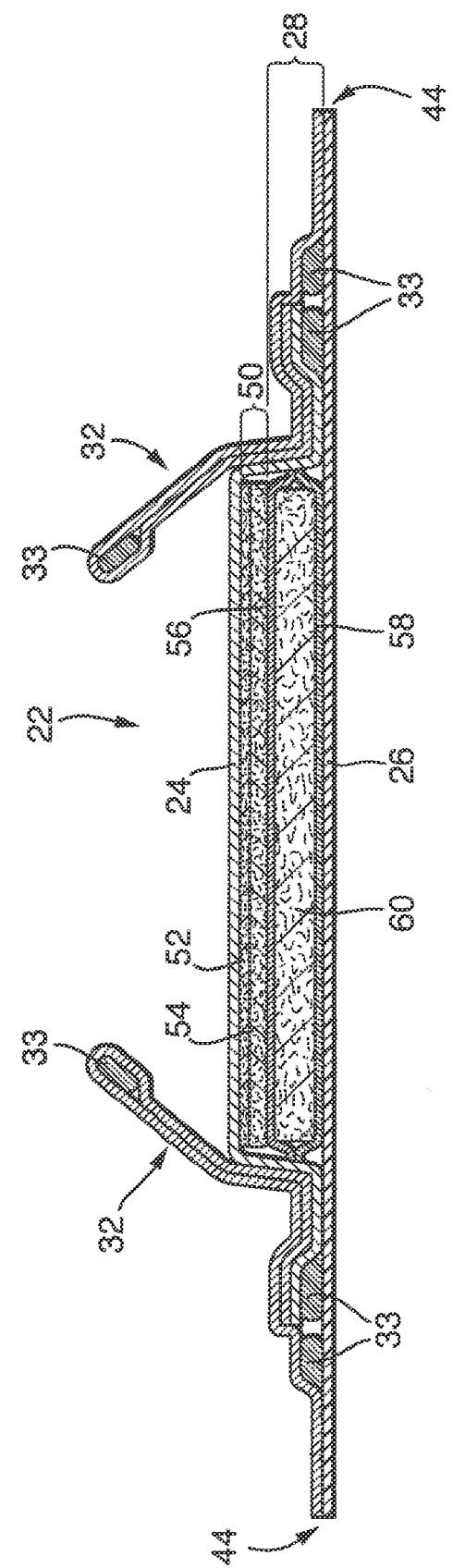
FIG. 2 shows a cross-sectional view of the disposable diaper of FIG. 1.

An exemplary absorbent structure is depicted in FIGS. 1 and 2. FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may include a portion of an absorbent core 28 encased between the topsheet 24 and the backsheet 26. The chassis may also include most or all of the absorbent core 28 encased between the topsheet 24 and the backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (elastic waist feature 34). The crotch region 37 is that portion of the diaper 20 which, when the diaper 20 is worn, is generally positioned between the wearer's legs. The diaper 20 is depicted with its longitudinal axis 100 and its transverse axis 110. The periphery of the diaper 20 is defined by the outer edges of the diaper 20 in which the longitudinal edges 44 run generally parallel to the longitudinal axis 100 of the diaper 20 and the end edges 46 run between the longitudinal edges 44 generally parallel to the transverse axis 110 of the diaper 20. The chassis also comprises a fastening system, which may include at least one fastening member 40 and at least one landing zone 42.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIGS. 1 and 2 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The absorbent core 28 in FIG. 1 generally is disposed between the topsheet 24 and the backsheet 26. In addition to the absorbent sandwich structure as described herein below, the absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 28 may comprise a liquid storage region 60, and other liquid handling elements 50, such as acquisition layers 52 and/or distribution layers 54. The absorbent core 28 may further comprise minor amounts (typically less than 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The diaper 20 may also include such other features as are known in the art including front and rear ear panels, waist cap features, elastics and the like to provide better fit, containment and aesthetic characteristics. Such additional features are well known in the art and are e.g. described in U.S. Pat. No. 3,860,003 and U.S. Pat. No. 5,151,092.

In order to keep the diaper 20 in place about the wearer, preferably at least a portion of the first waist region 36 is attached by the fastening member 42 to at least a portion of the second waist region 38, preferably to form leg opening(s) and an article waist. When fastened, the fastening system carries a tensile load around the article waist. The fastening system is designed to allow an article user to hold one element of the fastening system such as the fastening member 42, and connect the first waist region 36 to the second waist region 38 in at least two places. This is achieved through manipulation of bond strengths between the fastening device elements. Diaper 20 according to the present invention may be provided with a re-closable fastening system or may alternatively be provided in the form of pant-type diapers.

The embodiments of absorbent structures according to the present invention comprise a laminate structure, generally also referred to as a "sandwich" structure.

This refers to a design with two essentially flat outer layers, which are web materials or cut pieces of such web materials, as may be core web materials such as tissues, woven or non-woven materials made from hydrophilized polymeric materials and the like.

One preferred material is a so called SMS material, comprising a spunbonded, a meltblown and a further spunbonded layer. Highly preferred are permanently hydrophilic nonwovens, and in particular nonwovens with durably hydrophilic coatings. An alternative preferred material comprises a SMMS-structure.

The top layer 56 and the bottom layer 58 may be provided from two or more separate sheets of materials or they may be alternatively provided from a unitary sheet of material. Such a unitary sheet of material may be wrapped around the storage layer 60 e.g. in a C-fold.

Preferred non-woven materials are provided from synthetic fibers, such as PE, PET and most preferably PP. As the polymers used for nonwoven production are inherently hydrophobic, they are preferably coated with hydrophilic coatings. A preferred way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven as described in co-pending European patent application EP-A-1403419.

The storage layer 60 is positioned between the two layers of web material and comprises a particulate material, in particular the above mentioned superabsorbent materials. Typically, these are in irregularly shaped or spherical granules, which can swell upon contact with liquids, such as urine. Whilst this material may be in various shapes or forms, such as granular, spherical, flakes, fibrous, it will often consist of irregularly shaped particles, having a mean particle size of from 10 µm to 1000 µm, preferably with less than 5% by weight having a particle size of 5 µm, and preferably with less than 5% by weight having a particle size of more than 1200 µm.

It has been found beneficial to use a particulate absorbent polymer material for absorbent cores made in the present invention. Without wishing to be bound by theory it is believed that such material, even in the swollen state, i.e. when liquid has been absorbed, does not substantially obstruct the liquid flow throughout the material, especially when the permeability as expressed by the saline flow conductivity of the absorbent polymer material is greater than 10, 20, 30 or 40 SFC-units, where 1 SFC unit is $1 \times 10^{-7}$ $(cm^3 \times s)/g$. Saline flow conductivity is a parameter well recognized in the art and is to be measured in accordance with the test disclosed in EP 752 892 B (Goldman et al; P&G).

When employing such sandwich structures, there are a number of partly contradicting requirements, which these structures have to satisfy for an acceptable performance.

Thus, the particulate material is preferably immobilized. This refers to maintaining the arrangement of these particles in the structure during production as well as during use. In modern articles, the absorbency requirements in different parts of the article can be very different, such that for example more absorbency and hence absorbent material may be required in the proximity of the loading point than further away. Once the product design criteria have defined the absorbency distribution profile, this should be produced and maintained throughout the use cycle of the article, and in particular during use.

Further, the particulate material should be enabled to swell unrestrictedly. Even modern absorbent material such as described hereinabove exhibit absorbency properties depending to a certain extent on the pressure exerted on them. This pressure may be a regular use-pressure, such as when the baby as a user sits on the article. However, such a pressure may be created in sandwich structures, when, for example, the outer web material layers 56 and 58 are tightly bonded to each other in a way which does not allow expansion, thusly reducing the absorbency properties of the structure.

A further important requirement relates to the distribution of liquid throughout the structure, both longitudinally (length wise or x-directionally) and laterally (cross- or y-directionally), but also along the thickness or caliper (or z-direction) of the structure.

As discussed in the background section, it is known to arrange particles in an absorbent laminate or sandwich structure, with particulate absorbent material arranged in particular pattern designs. The present invention is aiming at producing a particular pattern under favorable production conditions.

Figure 3A:
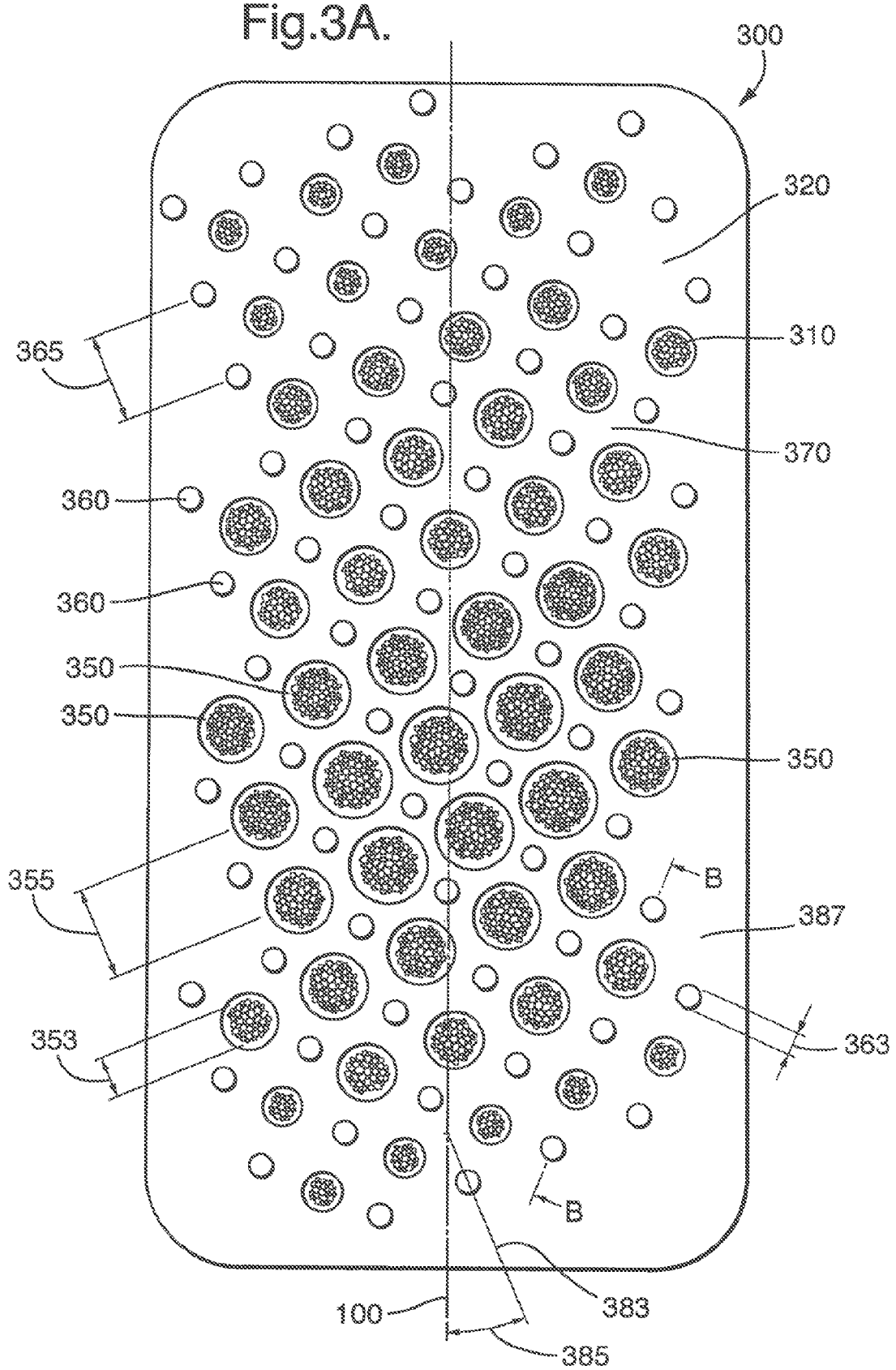
FIG. 3A shows a top view of an absorbent core sandwich structure.

It has been found, that in particular for sandwich structures intended for liquid handling purposes, such for the use in absorbent structures, advantages for liquid handling properties can be realized, when the structure is designed such that a cluster of particulate material is not fully separated from a neighboring cluster by a bonding line or region. An exemplary structure is exhibited in FIG. 3, showing a sandwich structure 300 comprising a particulate material 310 sandwiched between a carrier material 320 and a cover material 330. Further, the particle clusters 350 are depicted as well as bonding point regions 360 and channel regions 370 between neighboring clusters.

It further has now been found, that it is of particular benefit that between adjacent clusters there is a bonding zone, which is essentially free of any particles, thusly allowing a good bond between the carrier layers, such as through gluing, or other means.

Nonetheless, the structure should enable good immobilization or the absorbent particles, in particular when these are wetted. In particular, the absorbent structures or the absorbent article comprising such structures should provide more than 50% preferably more than 60%, even more preferably more than 80% and most preferably more than 90% when tested in the Wet Immobilization Test, such as described in EP1447066 (Busam et al.; P&G).

A pattern of particulate material is considered to comprise a plurality of particle clusters 350, each comprising a plurality of particles 310.

Such a particle cluster (refer to FIGS. 3 A and B) may comprise as few as about 10 particles, but may also be up to several hundred or even several thousands of particles. The particles may be arranged essentially in a "monolayer" sandwich structure, or multi-layer structures of essentially constant thickness, or may have varying thickness. This thickness may be expressed in terms of number of overlaying particle layers, or may be expressed by a local or an averaged basis weight, referring to the weight of particles for a given unit area. The skilled person will readily realize, that even a "local" basis weight will need a certain amount of averaging. However, when the basis weight in a given region is by design not constant over this region, such as may be with an increase towards the centre of the region in case of a heap or pile of granular material, the basis weight distribution may be approximated by a smoothed curve when following a cross-sectional view through this heap. Alternatively, the basis weight of a region may be designed to be constant throughout the region, such that an average basis weight for this region can be determined, optionally together with certain variability thereof. The basis weight of the neighboring regions can be the same, but is not required to be so. Typical basis weights as averaged over a particle cluster range from 10 g/m² or even less to 500 g/m² or even 1000 g/m². Typical basis weights averaged over a pattern (i.e. including both particle cluster and the regions between these clusters, which can be essentially free of particles) range from 1 g/m² to more than 400 g/m² or even more than 800 g/m².

A cluster 350 may have various forms and shapes, such as oval or elliptic or may be irregularly shaped. In a preferred embodiment these clusters are essentially circular. A cluster may have a diameter 353 of more than 2 mm, preferably more than 4 mm, but less than 20 mm, preferably less than 8 mm. The distance 355 between two neighboring clusters in a pattern 380 may be more than 2 mm, preferably more than 5 mm, but less than 30 mm, preferably less than 15 mm, and even more preferably less than 7 mm.

A plurality of clusters is forming a primary pattern wherein the clusters are spaced apart in any geometric way. Such a pattern may comprise as few as two clusters, but will typically comprise more than ten clusters. Often, it will comprise less than 1000 clusters. Any plurality of cluster may form regular or irregular sub-patterns of the primary pattern. The clusters may be discrete or disconnected regions, such that each of these regions is essentially circumscribed by a region which is essentially free of particles. These particle free regions do not need to be identical to the bonding regions.

Typically, the particles are arranged to be in direct contact to each other, i.e. each particle will be in contact with at least one other particle. It may, however, also be the case, that they do not contact each other. Then however, the distance between neighboring particles within a cluster will generally be less than the distance of neighboring particle clusters within the primary or sub-pattern.

Whilst the patterns are formed in an essentially continuous arrangement, there will be a certain repetition of the pattern, which will allow the same pattern to repeat in subsequent articles. Thus, the term "macro-pattern" refers to such a repeating pattern each of which may form an element of such an article.

Any of these discrete regions may be arranged in a macro pattern, such as being formed by at least two discrete regions forming a repeating pattern with varying, and generally larger continuous regions there between.

A pattern may be described by a characteristic axis, such as indicated by axis 383 in FIG. 3. Preferably, this axis is angularly offset to the longitudinal axis 100 of the diaper 20 or of the absorbent core respectively.

The bonding regions 360 between the clusters are preferably distinct regions rather than continuous regions, which would prevent channel regions 370 to be formed between the clusters. The bonding points may have varying shape and dimensions. In a preferred embodiment, the bonding regions 360 have a circular form of a diameter 363 of not less than about 1 mm, preferably not less than 2 mm, or even not less than about 5 mm. Further, the bonding point region diameter is preferably less than about 20 mm, preferably less than about 10 mm. The distance 365 of adjacent bonding points is primarily defined by the cluster pattern and may be not less than about 5 mm, preferably not less than about 10 mm, but less than about 20 mm, preferably less than about 15 mm.

A pattern can be unitary or can consist of sub-patterns; each of these sub-patterns may have different dimension or distances, respectively. The transition between sub-patterns may also be a gradual one. A pattern should be repeatable for subsequent absorbent structures for, e.g., a diaper.

In addition to the bonding regions 360, there may be a peripheral bonding 387, so as to seal the sandwich structure at the longitudinal or end edges.

Process for Producing Patterned Sandwich Structures

In a particular aspect, the present invention relates to a method of producing a sandwich structure having a pattern of particulate material enveloped between a carrier material.

Such a process should allow a very precise and repeatable production of the pattern at high or very high production speeds, i.e. preferably not being the overall speed production limiting process step in the overall production process, which may be up to 0.5 msec but often are 10 msec or even higher. Even further, the process should enable robust and inexpensive equipment designs.

Thus, the present invention relates to an essentially continuously operated lay-down of particulate material onto a surface, which is moveable at a preset surface speed, in a predetermined pattern. The pattern consists generally of regions comprising particulate material, and regions being essentially free of particulate material.

A schematic representation of the process can be seen in FIG. 4, showing a particulate material supply 410, supplies 420 and 430 for carrier material 320 and cover material 330 respectively, a carrier support means 470, and the optional element of a particle transfer devices 440. Also shown is the resulting sandwich structure 300 with the particulate material 310 between carrier material 320 and cover material 330.

The particulate material is generally supplied to the process from a particle storage system, and generally will be supplied in bulk form. Bulk refers to the fact, that the multitude of particles may be described by properties and parameters relating to an individual particle, such as composition, size, shape, particle density, and so on, but also by properties and parameters relating to a multitude of such particles, such as bulk density, particle size distribution, or flow properties.

The particulate material is deposited on a moving surface of a web material. Thusly, the process may exemplary be described to position particles from a bulk storage system in a regular pattern onto a web material.

Such processes require not only an accurate positioning of the particulate material, but should be compatible with high of even very high "converting" speeds, which correspond within the current context generally to the speed of the moving surface.

Many current particle deposition systems as described in the background section hereinabove are generally very speed dependent, and either create unacceptable losses or variability with regard to positioning and applied weights when being run at such speeds. EP Patent No. 1,621,165, which is incorporated herein by reference provides a solution for the aforementioned difficulties by providing a method for indirectly applying absorbent gelling material granules onto a carrier layer for use in an absorbent article, particularly a diaper, wherein particulate granules are taken up by a transfer device from a bulk storage. Referring to FIG. 4, the transfer device 440 has recesses 452 on the surface, wherein the number, size and position thereof determine the amount and pattern of superabsorbent particles 310 taken up by the transfer device 440. The transfer device 440 is moveable from a loading position 442 adjacent to the bulk storage 410 to a discharging position 448 at which the carrier layer 320 is adjacent to the transfer device. The transfer device further has a means 444 for retaining the superabsorbent particles inside its recesses during movement of the transfer device 440 to the discharging position 448, and a means 446 for expelling the particles onto the carrier layer at the discharging meeting position 448. Preferably, these means are vacuum and blow off air, respectively.

The present invention provides a method for creating a pattern of a particulate material sandwiched between a carrier material by depositing a pre-metered amount of the particulate material 310 on a carrier web 320, which forms a particular pattern of indentations 328, i.e. which is deformed out of the flat plane. This is achieved by placing the carrier material 320 on a carrier support structure 470 forming a particular pattern. Between the structure elements 475 forming this pattern there is essentially free space allowing the carrier web to bulge into this space upon drawing forces, such as may be accomplished by a vacuum suction 472 generating a gas (air) flow through the fluid or air permeable carrier material 320. The particulate material 310 is then positioned in these indentations, thusly forming a cluster 350, and may fill these indentations partly, completely or may over-fill these, such as by forming a "heap". In any of these cases, at least a part of the carrier material is essentially free of particulate material. This area is referred to as the bonding region 360, which may correspond to the carrier support area 322, or which may be larger or smaller than this.

The formation of the sandwich structure is completed by covering the patterned particulate material of the indentations 350 with a cover material 330 and fixing the two web materials to each other, such as by applying adhesive material 495 at least to the bonding region of the carrier material or to the corresponding area of the cover material.

According to the present invention, the carrier material 320 is positioned onto a carrier support means 470. The carrier support means 470 comprises a surface, which may be brought into contact with the carrier material at a matched speed. Such a match is achieved, if the surface moves with a speed which corresponds to the overall process speed.

The carrier support means may be of cylindrical shape rotatably positioned around its longitudinal axis. The outer cylindrical surface such as the shell 450 of a rotating drum will then form the support region for the carrier material. The carrier support means may also comprise an essentially endless moveable belt carried upon a system of transporting rollers.

The carrier material 320 will be positioned on the "outer" surface of the carrier support means, outwardly referring to the outer surface of a drum, or to the surface opposite to that surface of a moving belt, which is in contact with the majority of the belt support rollers.

The carrier web will be positioned onto the carrier support area 477. This sub-region of the carrier support means is the area, which is in contact with the carrier web, when this is positioned in an essentially untensioned state onto the carrier. Thus, if the carrier support means were a continuous (unapertured) drum, the carrier support area would be the cylindrical surface. It the carrier support means were an apertured drum, the carrier support area would be the area of the cylindrical surface minus the area of the apertures. If the carrier support means were a square grid formed into a cylindrical shape, the carrier support area were the outwardly facing areas of the ribs of the grid.

Figure 5A:
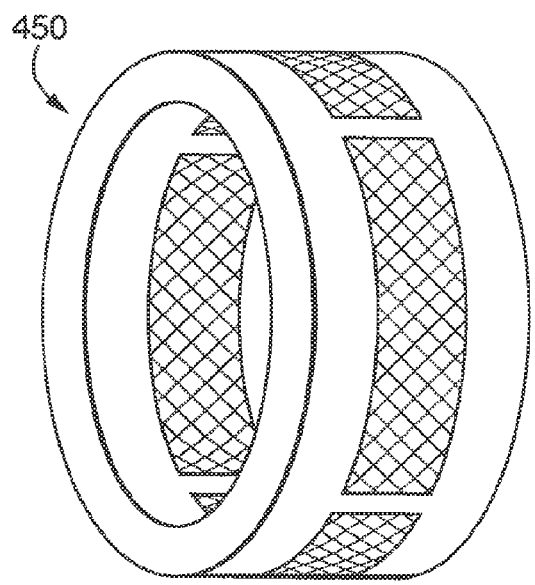
FIG. 5A is a schematic perspective presentation of the shell of a carrier support means.
Figure 5B:
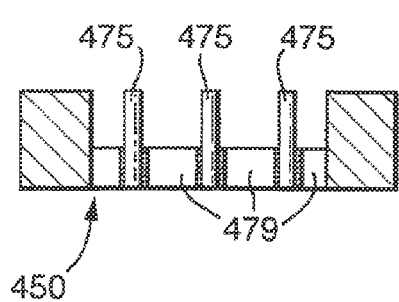
FIG. 5B is a schematic cross-sectional view of the shell of FIG. 5A.
Figure 5C:
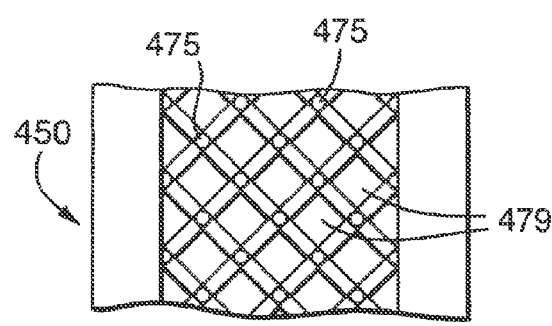
FIG. 5C is a schematic top view of a part of the shell of FIGS. 5A and B.
Figure 6A:
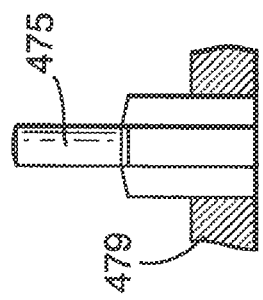
FIGS. 6 A, C, E, and G show various embodiments of a carrier support means, and FIG. 6 B, D, F, H corresponding cross-sectional views.
Figure 6B:
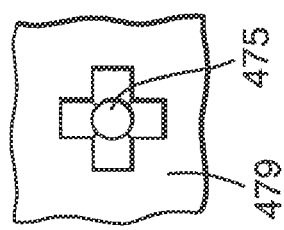
Figure 6C:
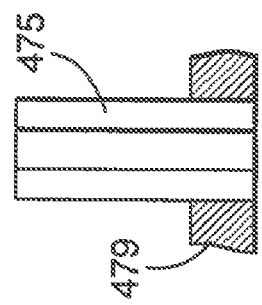
Figure 6D:
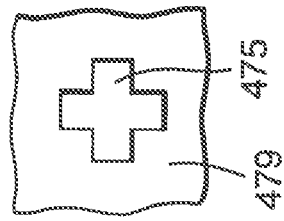
Figure 6E:
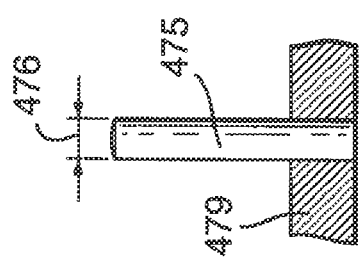
Figure 6F:
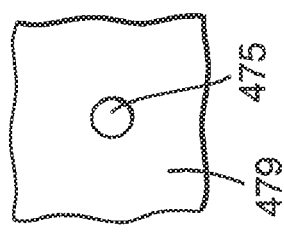
Figure 6G:
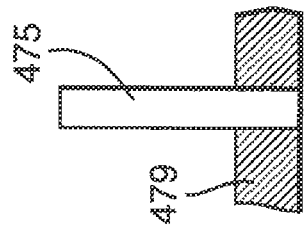
Figure 6H:
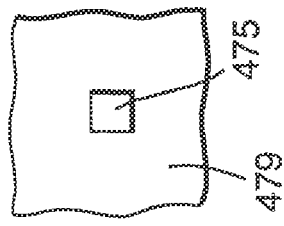

In a preferred embodiment, the carrier support area is not a continuous region, i.e. the carrier support area can be represented by "islands", such as may be created by pins 475 protruding of the cylinder shell 450 (FIG. 5). The outermost surface covering the outward end points of the pins 475 corresponds to the carrier support area 477. The support pins may have a rectangular cross-section. In a preferred embodiment, the support pins have a cylindrical shape, having a diameter 376 of preferably more than 1.5 mm, more preferably of more than 5 mm, but not more than 15 mm, more preferably of not more than 10 mm. If the outermost surface of the pins is not a flat surface (see FIG. 6 A, B), but for example has a rounded, oval or circular cross-sectional shape (see FIG. 6C, D), the area referred to is the projection to the area as would be covered by the carrier web support material in an essentially untensioned state. The carrier support area may also be formed by ridges, which may be straight or curved, or in the form of a cross (see FIG. 6E, F). The carrier support area may be formed by "hybrid" structures, such as pins protruding out of a grid or a cross, or a grid having varying heights, such that, for example the intersections points of the grip form the most outward oriented areas (see FIG. 6 G, H).

Thus, the carrier web means is intended to be supported by the (most outwardly) oriented carrier support area, but it may bulge or deform radially inwardly in the area other than the carrier support area by mechanisms as described herein below.

However, for certain designs, it may be appropriate to support the carrier material not only at the outer enveloping surface, but to also support the carrier material in a secondary support area. Such an area can be compared with "low level islands", which do not have contact with the carrier material if applied without deforming forces, but which will contact this only upon a certain deformation (inward bulging) of the web, and then support it. For example, there can be one set on carrier support pins having a certain height so as to form the primary carrier support area, and a second set of pins having a lower height so as to form the secondary support area (see also FIG. 6 G, H).

The carrier support area will form a particular, predefined pattern. This pattern corresponds to the desired particulate material pattern in the sandwich structure. Preferably, it has a macro pattern generally along the x-direction of the web running over the carrier web support means, but arranged at a predefined angle (see FIG. 5C). This may be repeating, and will typically reflect the pattern of the patterned absorbent sandwich structure.

The dimensions of the carrier support area should further be adapted to the overall properties of the carrier material. For example, when using support pins, the support area of an individual pin should not be below a critical area, under which the local stress in the web might cause destructive deformation, or penetration of the pin through the pores of the web.

These pins may be positioned at distances to the next neighboring pin of 5 mm or the distance may be 20 mm or more. These pins may have a cylindrical shape. In order to avoid damaging of the supported web material, each individual pin should have an essentially outwardly facing surface of at least 3.5 mm$^2$, preferably 10 mm$^2$, but not more than 40 mm$^2$. The pins may also have a non-cylindrical shape at the outwardly facing tip, which is in contact with the web. The contacting area will then be considered to be the projection of the part of the tip being in contact with the carrier material upon deformation to a plane as formed by the carrier material in an untensioned state. Alternatively or in addition, the carrier support pattern may also be in the form of another geometrical pattern, such as by elongated pins, or ribs or ridges, which may be straight or curved. Preferably, these do not form a continuous pattern; however two or more ribs may be connected, for example forming a cross-shaped support area. The carrier material has to satisfy the requirements for the final resulting structure, such as liquid handling properties in the case of fluid handling applications.

Further, the carrier material has to have the ability to deform under forces as applied during the process. Whist these forces can by of various types, the most preferred one is the drag force resulting from applying a fluid flow through a fluid permeable carrier material. In a particularly preferred embodiment, the carrier material is air permeable, such by being an apertured film material or even more preferable a fibrous web.

The air permeability is connected to the material pore size and thickness, and hence—in the case of fibrous materials—to the intrinsic density of the fiber material and the diameter of the fibers, respectively the diameter distribution in case of fibers having varying diameter. Further the carrier material has to have the ability to retain particles as deposited thereon.

This may be related to the permeability of the carrier material, as the above mentioned pore size may allow small particles to pass through. Whilst this is not desired in principle, a certain amount of "fines" can be accepted to pass through. This may be then be recovered downstream.

Important for the present invention are the deformation properties of the carrier material. Deformation refers to the ability to elastically (i.e. essentially recoverably) or plastically deform upon application of forces as exerted by the carrier web deformation and fixation means.

As the most carrier materials for the present invention will be essentially two-dimensional webs having an machine, longitudinal, or x-directional extension and a cross-machine, transversal, or y-directional extension perpendicular to the first.

Upon application of a force in any directions, the material will elongate along this direction. Thereby, the material will tend to compensate for this elongation by reducing its flat dimension perpendicularly to the direction of the direction of the force, as well as its thickness along the z-direction. Typically, web materials are described by their properties measured along the machine direction (MD) as well as in cross-direction (CD), such by creating stress-strain profiles and/or defining certain characteristic points of these profiles. Typically, such properties are determined by clamping a stripe of the material and applying pull forces to the clamp. The carrier material can further be characterized by its mechanical properties, namely its CD- and MD-extensibility at certain loads, such as may be determined by conventional stress-strain measurements using line clamps at a crosshead speed of 0.127 m/min. Preferably, the ratio of CD to MD elongation is more than 1 to 0.2, but preferably not more than 1 to 2.

As will be described herein below, useful carrier materials will be submitted to a force as may be generated by a fluid flow through the materials, such that a force in z-direction will be applied. However, as the carrier material is supported in the carrier support area, such as by carrier support pins, the deformation in this case will be determined by the CD- and MD-deformation properties. Henceforth, these properties have to be adjusted to the support area pattern.

The carrier material will be temporarily affixed to the carrier support means and will be deformed out of its flat/plane arrangement by the material holding means. Whilst a multitude of physical principles may be used, such as magnetic forces in case of magnetically responding materials, a particularly preferred embodiment relies on the use of fluid flow through the web.

To this end, the carrier support means may comprise a vacuum suction means 472, arranged such that gas—in particular air—is drawn through the web material. Based on the flow resistance due to the porosity of the web, the flow will induce a force in the z-direction, and thus deform the unsupported parts of the web.

Consequently, the web will form an indentation 328 (see FIG. 4B), the upper points will be defined by the support area (e.g. the support pins), and the "bottom of the valley" will be defined by the ratio of vacuum suction force, permeability and stress-strain properties of the carrier material. Thus, if an essentially homogeneous material would have the same properties in MD- and CD-direction, and—for example—the web support structure would consist of support pins arranged in a quadratic arrangement, the indentation would form a trough with its deepest points in the centre of the square.

Defining a space curve to connect two points of the squarely arranged support pins to follow the deformation of the web material will generally result in longer curve lengths than the linear distance of these support pins, and if the curve connects two diagonally opposed points, the space curve will have the longest length, generally following a shape which can be approximated by a hyperbolic curve.

Similarly defining an outer surface by connecting the support area—i.e. in the present case the square connecting the four corner points of the support pins, and thus the area of the web covers before applying the suction forces—this can be compared to the actual surface area of the deformed material forming the indentation.

Similarly, a volume can be defined for the indentation formed by the deformed carrier material, which is circumscribed by the deformed web material and the surface as covered by the web material prior to deformation through the deformation means. Preferably, this volume is at least 30 $mm^3$, preferably at least 100 $mm^3$, but less than 1000 $mm^3$.

This "indentation volume" can be compared to the volume of the particles, which are to be positioned therein. Depending on the design target, the volume of the particles of a cluster may fill more than 5% of the volume of the indentation, or more than 50% of the volume. In the case of "overfilling" (or forming a heap), the indentations will typically not be filled by more than 150% of their volume.

After the carrier material 320 has been deformed to form the indentations 328 and the particulate material 310 has been positioned in or on these indentations, the structure is covered by a cover material, typically a web material, too. This cover material is primarily defined by the requirements of the final application. It may be the same material as the carrier material, and may be unitary with the carrier material, such as when then particulate material is deposited in a region—such as the centre stripe region—of a web material and laterally outwardly oriented part or parts of the material are then folded over such as along a longitudinal fold line, so as to cover the particulate material.

It may also be the same kind on material, but being supplied separately, or it may also be a different material, which is suitable for the intended application as well as for being bonded to the carrier material.

The carrier material and the cover material are connected to each other, such as permanently bonded so as to form the composite sandwich structure with the particle pattern between. This bonding can be achieved by conventional means, such as adhesives, or thermo bonding or the like.

It has been found important, that the bonding is not impeded by particles positioned between the webs in the bonding regions. Bonding regions refers to regions, which are essential for ensuring good permanent bonding. Thus, in the above described example of support pins forming the support area, the bonding region will generally coincide with this area, but may be somewhat smaller or larger than the support area.

For example, when spray applying adhesives, it might be preferable to have a bonding area of more than 2%, preferably of more than 7%, but less than 50% of the total pattern area. The bonding area may be larger than the support area, which will typically be the case when the indentations are not completely filled with particulate material. If applying melt fusion bonding at the support pins, the bonding area might be as little as 50% of the support area.

Thus, the bonding region is preferably essentially free of particulate material. The term "essentially free" refers to the fact that any particles present in this area should not lead to break up of the bonding under normal use conditions.

However, if the particulate material exhibits a broad particle size distribution profile, or if particle break up is created during the process, a certain amount of "dust" is acceptable in this regions. A method of assessing the amount of "bonding region particle loading" is described hereinafter for the application of absorbent materials.

After having described the elements required for executing the present invention, the following will describe the individual process steps.

Overall, it is assumed, that a sandwich structure is to be produced comprising particulate material in a predefined pattern. The process is an essentially continuous process, starting from essentially endless web materials and combining these with particulate materials as provided in bulk supply form. The resulting continuous sandwich composite may be separated, such as by cutting, into individual pieces, each comprising at least a macro pattern of the particulate material sandwich.

The individual process steps are now explained in more detail. The order does not necessarily reflect a chronological order for these steps.

a—An essentially flat web material is provided to serve as carrier material and/or as cover material forming the outer sandwich layers. Thus, the web material may be unitary forming both outer sandwich layers such as by longitudinal folding. There may also be two different web materials, one forming the carrier material, and the other the cover material. In a preferred execution, the web materials are separate, but of the same type. The properties of the web materials have to be compatible with the indented use. In addition and in a preferred embodiment, the carrier material is permeable for gas, such as air, but not for particles. In a preferred embodiment, the web materials are nonwoven materials, and more preferably a combination of a spunbonded layer (S) with a meltblown layer, so as to form a SMS or more preferably a SMMS type web.

b—An essentially endless web support means for the carrier having a support pattern is provided, preferably a rotatable drum with the support pattern being on the outer cylinder or shell surface of this drum. Preferably, the carrier support pattern is formed by carrier support pins. Such pins extend towards the outer surface of the carrier support means, which then can generally be described by enveloping the outwardly facing areas of theses pins.

c—In order to first hold the carrier material and to then form indentations therein, a carrier material holding means is actuated. In the preferred embodiment of the carrier means being a rotating drum respectively the rotating shell of a drum, and the carrier material is a an air permeable material which is positioned on this shell, the carrier material holding means may be vacuum suction inside the drum. This may be achieved by non-rotating vacuum boxes underneath the surface of the drum. Thereby, air is sucked through the carrier material in this section, thereby exerting forces on the web, thusly holding it affixed on the surface of the drum and deforming it in unsupported regions. The amount of suction, i.e. the degree of vacuum created depends on the permeability properties of the web, the unsupported area, and the desired deformation (i.e. the size of the indentations).

d—The carrier material is guided towards the outer surface of the carrier web support and deformation means at a match speed, e.g. the carrier material moves at a carrier speed of more than 0.5 msec, more preferably more than 5 msec, matching the radial outer surface speed of the carrier support drum.

e—As a further process step, a particulate material is provided, such as conventional superabsorbent particles. Preferably this material is provided in bulk form, such as in a hopper.

f—This material is metered and dosed according to the requirements in the resulting product. This dosing may be constant over time or variable. In a preferred embodiment, the dosing already pre-forms a particle cluster in a particular pattern, as may be desirable for the resulting product.

g—The particulate material is then transferred to the outwardly facing surface of the carrier material, or the receiving surface of the carrier material, while this is supported by in the web support areas on the web support means, and deformed in to indentations in the unsupported regions.

h—Further, a sandwich fixation means is actuated for affixing the carrier material and the cover material while the particle pattern is maintained. In a preferred embodiment, the fixations means is application of spray glue before and/or after the particles are transferred onto the carrier material. In case of carrier and cover web having matching melt properties, the bonding means may also be heat fusion bonding, such as by ultra-sound. The carrier and cover webs are affixed to each other in the bonding area. The bonding area can be described by at least covering the web support area, but will typically extend longitudinally and laterally outwardly of this region, thusly covering an area of more than 2%, preferably of more than 7%, but less than 50% of the support region. Preferably, the bonding area is preferably essentially free of particles. This requirement can be assessed by using the method for determining particles in the bonding area, as described in the method section herein below. Optionally, the bonding means may also be applied to the particles.

i—After the particles are positioned on the carrier material the cover material is applied and bonded to the carrier material, thereby closing the sandwich structure. This is a preferred but optional step. In accordance with the present invention a sandwich structure comprising a carrier material but no cover material can be provided, as the sandwich fixation means can provide sufficient integrity to the structure and make it a sandwich-like structure, such that it is unnecessary to further provide a cover material.

During this process, it is important, that the carrier web is supported only in the support pattern region of the web support means, and that the carrier material is deformed by the carrier holding means such that indentations are formed in the unsupported regions. This forms a primary pattern, optionally comprising sub-patterns. The pre-metered particulate material is preferably deposited essentially exclusively in these indentations, preferably thereby filling at least 5% of the indentation volume, preferably filling not more than 150% of the indentation volume.

Method for Determining Absence of Particles in Bonding Area

The test has the purpose of assessing the bonding areas with regard to contamination of particulate material, in particular of superabsorbent material.

A test solution is prepared by diluting 1.5 g of purple bromocresol indicator (CAS number 115-40-2) in 10 l of de-ionized water, and adding 4 ml of 1 mol/l hydrochloric acid (1 N HCl). The test specimen is wetted by the test solution, e.g. by using a pointed pipette and adding the solution drop wise, or by using a fine spray bottle. The amount of added test liquid will depend on the size of the sample and the amount of superabsorbent material. It should be sufficient to wet all particles in the considered region so as to ease visual counting, which is then performed on the respective regions. The assessment may also be supported by employing a magnifying glass or a microscope with suitable magnification. Very fine particles also referred to as dusts, and generally having a size corresponding to the pore size of the carrier and/or cover material, are not counted.

A region is classified as being "free of superabsorbent particles", if less than two particles are detectable. A region is classified as being "essentially free of superabsorbent particles", if particles present in the bonding area do cover more than about 50% of this area.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing a sandwich structure comprising a pattern of particulate material, the method comprising the steps of:
   advancing a carrier material to a carrier support structure, the carrier support structure comprising a shell and a carrier support area, wherein the shell defines an outer circumferential surface, and wherein the carrier support area protrudes radially outward from the outer circumferential surface of the shell;
   rotating the carrier support structure;
   advancing the carrier material onto the carrier support structure, wherein the carrier material defines a support region and an indentation region, wherein the carrier material is supported by the carrier support structure in the support region and is unsupported by the carrier support structure in the indentation region;
   rotating a transfer device to a loading position, wherein the transfer device comprises recesses;
   metering a particulate material into the recesses of the transfer device;
   rotating the transfer device to a discharging position;
   transferring the particulate material into the indentation region of the carrier material;
   advancing a cover material adjacent to the carrier material; and
   bonding the cover material to the carrier material in the support region of the carrier material, wherein the particulate material is sandwiched between the carrier material and the cover material.

2. The method of claim 1, wherein said carrier material is a non-woven material selected from the group consisting of SMS type and SMMS type.

3. The method of claim 1, wherein said carrier material has a CD-extensibility or a MD-extensibility of more than about 20%.

4. The method of claim 1, wherein said carrier material has a ratio of MD-extensibility to CD-extensibility at a given load of not more than one to two.

5. The method of claim 1, wherein said cover material is a non-woven material.

6. The method of claim 1, wherein said particulate material comprises superabsorbent particles.

7. The method of claim 1, wherein the step of bonding the cover material to the carrier material in the support region of the carrier material further comprises the step of thermal-bonding the cover material to the carrier material in the support region of the carrier material.

8. The method of claim 1, wherein the step of bonding the cover material to the carrier material in the support region of the carrier material further comprises the step of glue-bonding the cover material to the carrier material in the support region of the carrier material.

9. The method of claim 1, wherein the step of bonding the cover material to the carrier material in the support region of the carrier material further comprises the step of sprayed adhesive bonding the cover material to the carrier material in the support region of the carrier material.

10. The method of claim 1, wherein said carrier support area comprises a grid, wherein the grid comprises one or more ribs.

11. The method of claim 10, wherein said carrier support area comprises a portion of the outer cylindrical surface having a rectangular cross-section.

12. The method of claim 1, wherein said carrier support area comprises a cylindrical surface of the shell of the carrier support structure.

13. The method of claim 1, wherein the carrier support structure comprises vacuum air suction.

14. The method of claim 1, wherein the support region comprises a bonding region that is at least 2% of the support region.

15. The method of claim 14, wherein said bonding region is not more than 50% of the support region.

16. The method of claim 1, wherein said bonding region comprises essentially no particulate material, as assessed by the method for determining the absence of particles in the bonding area.

17. The method of claim 1, wherein said indentations have a volume of more than 30 mm$^3$.

18. The method of claim 1, wherein the particulate material fills more than 5% of the volume of said indentations.

19. The method of claim 1, wherein the particulate material fills not more than 150% of the volume of said indentations.

20. A method for producing a sandwich structure comprising a pattern of particulate material, the method comprising the steps of:

advancing a carrier material to a carrier support structure, the carrier support structure comprising a carrier support area and an indentation area, wherein the carrier support area comprise a plurality of discrete pins;

rotating the carrier support structure;

advancing the carrier material onto the carrier support structure, wherein the carrier material defines a support region and an indentation region, wherein the carrier material is supported by the carrier support area in the support region and the indentation area in the indentation region;

rotating a transfer device about an axis of rotation, wherein the transfer member comprise a recess;

metering a particulate material into the recess of the transfer member;

transferring the particulate material from the recess into the indentation area of the carrier material;

advancing a cover material adjacent to the carrier material; and bonding the cover material to the carrier material in the support region of the carrier material, wherein the particulate material is sandwiched between the carrier material and the cover material.

21. The method of claim 20, wherein the pins have a rectangular cross-section.

22. The method of claim 20, wherein the pins have a circular cross-section.

23. The method of claim 20, wherein the pins have a polygonal cross-section.

* * * * *